United States Patent [19]

Grenier

[11] Patent Number: 5,613,964
[45] Date of Patent: *Mar. 25, 1997

[54] SANITARY ARTICLE

[76] Inventor: Dyandra Grenier, 10101 E. County Rd. 350 South, Walton, Ind. 46994

[*] Notice: The term of this patent shall not extend beyond the expiration date of Pat. No. 5,429,631.

[21] Appl. No.: 446,437

[22] Filed: May 22, 1995

Related U.S. Application Data

[63] Continuation of Ser. No. 99,940, Jul. 30, 1993, Pat. No. 5,429,631, which is a continuation-in-part of Ser. No. 775,686, Oct. 11, 1991, abandoned.

[51] Int. Cl.⁶ .............................. A61F 13/15; A61F 13/20
[52] U.S. Cl. ...................... 604/385.1; 604/358; 604/378; 604/393
[58] Field of Search ..................................... 604/358, 378, 604/385.1, 393

[56] References Cited

U.S. PATENT DOCUMENTS 2,929,379  3/1960  Poulsen .
3,367,334  2/1968  Testa .
4,505,707  3/1985  Faeney .
4,765,477  8/1988  Fröidh et al. .
4,938,756  7/1990  Salek .
5,429,631  7/1995  Grenier .

Primary Examiner—John G. Weiss
Assistant Examiner—P. Zuttarelli
Attorney, Agent, or Firm—Laff, Whitesel, Conte & Saret, Ltd.

[57] ABSTRACT

A sanitary napkin assembly comprises a plurality of thin, substantially planar, individual sanitary napkin units which are arranged in a stack so that their planar faces are adjacent. Each individual napkin unit is removably attached to the one or two individual, units which are adjacent to it. Each individual napkin unit comprises a sheet or layer for receiving, absorbing, and containing; body fluids secreted by the user, and a water-proof barrier sheet or layer for precluding, leakage of absorbed fluids to adjacent units or to the user's clothing. Thin adhesive-tape strips (or other suitable attachment media) are used to permanently attach the fluid-receiving layer to the barrier layer. Similar tape strips (or other suitable attachment media) are used to removably attach individual napkin units to adjacent units, and to removably attach the assembly to an interior portion of the user's undergarment. The size and construction materials for the individual units are selected to allow disposal in a conventional water closet. In use, the uppermost individual napkin unit is exposed to the portion of the body to be protected. The exposed unit absorbs secreted body fluids. When the exposed unit becomes soiled, the user may remove that unit, thereby exposing a fresh unit for use.

24 Claims, 4 Drawing Sheets

SANITARY ARTICLE

CROSS-REFERENCE TO RELATED APPLICATION

This application is a continuation of application Ser. No. 08/099,940, filed Jul. 30, 1993; now U.S. Pat. No. 5,429,631, which is a Continuation-in-Part of my prior application Ser. No. 07/775,686 filed Oct. 11, 1991, now abandoned.

BACKGROUND OF THE INVENTION

This invention relates to sanitary articles for absorbing body fluids, and more particularly to sanitary articles worn by women for absorbing and containing body fluids produced during menstruation.

A number of sanitary articles have been developed for absorbing and containing body fluids produced during menstruation. A commonly-used type of sanitary article is the sanitary napkin which is worn between a woman's body and an undergarment to protect the undergarment and adjacent garments. A typical sanitary napkin consists of an inner layer of absorbent material which is worn next to the body, and an outer barrier layer which is worn between the absorbent layer and the user's undergarment. The outer barrier layer is constructed of a water-proof material to prevent fluid absorbed by the inner layer from leaking or spreading by capillary action to other garments.

Existing feminine sanitary napkins have a variety of significant disadvantages which cause discomfort and inconvenience for users. One problem with many existing napkins is that they lack adequate absorbent capacity to permit the user to wear the napkin for an acceptable length of time before replacing it with a fresh napkin. When the user's rate of fluid discharge exceeds the capacity of the napkin, the fluid may leak to and soil adjacent garments. This causes significant embarrassment and inconvenience for the user. Even when the absorbed fluid does not actually spread to another garment, some fluid may still be released from the layer back onto the user's body, causing discomfort and irritation. In addition, such body fluids may produce an undesirable odor when not properly contained.

In order to solve the capacity problem, sanitary napkins have been developed containing larger quantities of absorbent materials. A problem with such larger-capacity sanitary napkins is that they are relatively bulky. Such napkins are inconvenient for many users because their larger size makes them inconvenient to store, carry and apply. In addition, because of the additional absorbent material, they are generally thicker than previous napkins and their presence under the user's clothing is more difficult to conceal.

Another problem with significantly larger capacity napkins is that once the napkin has absorbed a substantial amount of fluid, it is difficult to prevent the napkin from releasing some of the absorbed fluid back to the user's body as the user goes about the normal activities of daily life. When the user conducts such dynamic activities as walking and bending over, the user's body may compress the absorbent layer, thereby forcing some of the absorbed fluid to be released. Thus, an increase in the amount of absorbent material in a napkin may not result in a proportional increase in either the capacity or the wear time in actual use.

In addition, special "super-absorbent materials have been developed which have higher absorbent capacity than previously used materials. Still other sanitary napkins have been developed with a top sheet to prevent the fluids, once absorbed, from being released again back to the user's body. However, these napkins still have a limited time of use and require relatively frequent replacement.

A further problem with existing sanitary napkins is disposal of soiled napkins and application of fresh napkins. Typically, sanitary napkins are constructed of materials which cause disruptions in normal plumbing systems and therefore cannot be disposed of in toilets. Thus, in almost every case, the user must dispose of the soiled napkin in an ordinary refuse receptacle. The problem of proper disposal of the soiled napkin causes embarrassment for some users. For example, when using a public restroom, the user may be unable to prevent others from viewing the user's disposal of the napkin. Users may also have health concerns in public facilities due to potential exposure to the discarded napkins of other users. When visiting the private home of another, the user may not wish to dispose of the napkin in a receptacle which is only occasionally emptied. Similar privacy problems attend application of fresh napkins.

OBJECTS AND SUMMARY OF THE INVENTION

It is therefore an object of the present invention to provide a sanitary napkin product which permits an extended period of wear.

It is another object of the invention to provide a sanitary napkin which allows disposal in conventional water closets.

It is a further object of the invention to provide a sanitary napkin product which allows a user to immediately make a fresh napkin available for use when an exposed napkin has become soiled.

It is another object of the invention to provide a sanitary napkin product which allows convenient removal of a soiled napkin and exposure of a fresh napkin even in situations in which minimal privacy is available.

It is a further object of the invention to provide a multiple unit sanitary napkin product which allows convenient removal of a soiled napkin with minimal damage to any remaining units.

A sanitary napkin assembly according to the present invention comprises a plurality of thin, substantially planar, individual sanitary napkin units which are arranged in a stack so that their planar faces are adjacent. Each individual napkin unit is removably attached to the one or two individual units which are adjacent to it. Each individual napkin unit comprises a sheet or layer for receiving, absorbing, and containing body fluids secreted by the user, and a waterproof barrier sheet or layer for precluding leakage of absorbed fluids to adjacent units or to the user's clothing. Thin adhesive-tape strips (or other suitable attachment media) are used to permanently attach the fluid-receiving layer to the barrier layer. Similar tape strips (or other suitable attachment media) are used to removably attach individual napkin units to adjacent units, and to removably attach the assembly to an interior portion of the user's undergarment. The materials for the individual units are selected to allow safe and convenient disposal in a conventional water closet (including modern, water-saving, 1.6 gallon-per-flush fixtures). Each individual unit may be flushed into a domestic plumbing system without damaging or clogging plumbing fixtures, drain lines, or sewers. In use, the uppermost individual napkin unit is exposed to the portion of the body to be protected. The exposed unit absorbs secreted body fluids. When the exposed unit becomes soiled, the user may remove and dispose of that unit, thereby exposing a fresh unit for use.

BRIEF DESCRIPTION OF THE DRAWINGS

These and other features of this invention will be best understood by reference to the following detailed description of a preferred embodiment of the invention, taken in conjunction with the accompanying drawings, in which.

DETAILED DESCRIPTION OF THE PREFERRED EMBODIMENT

Figure 1:
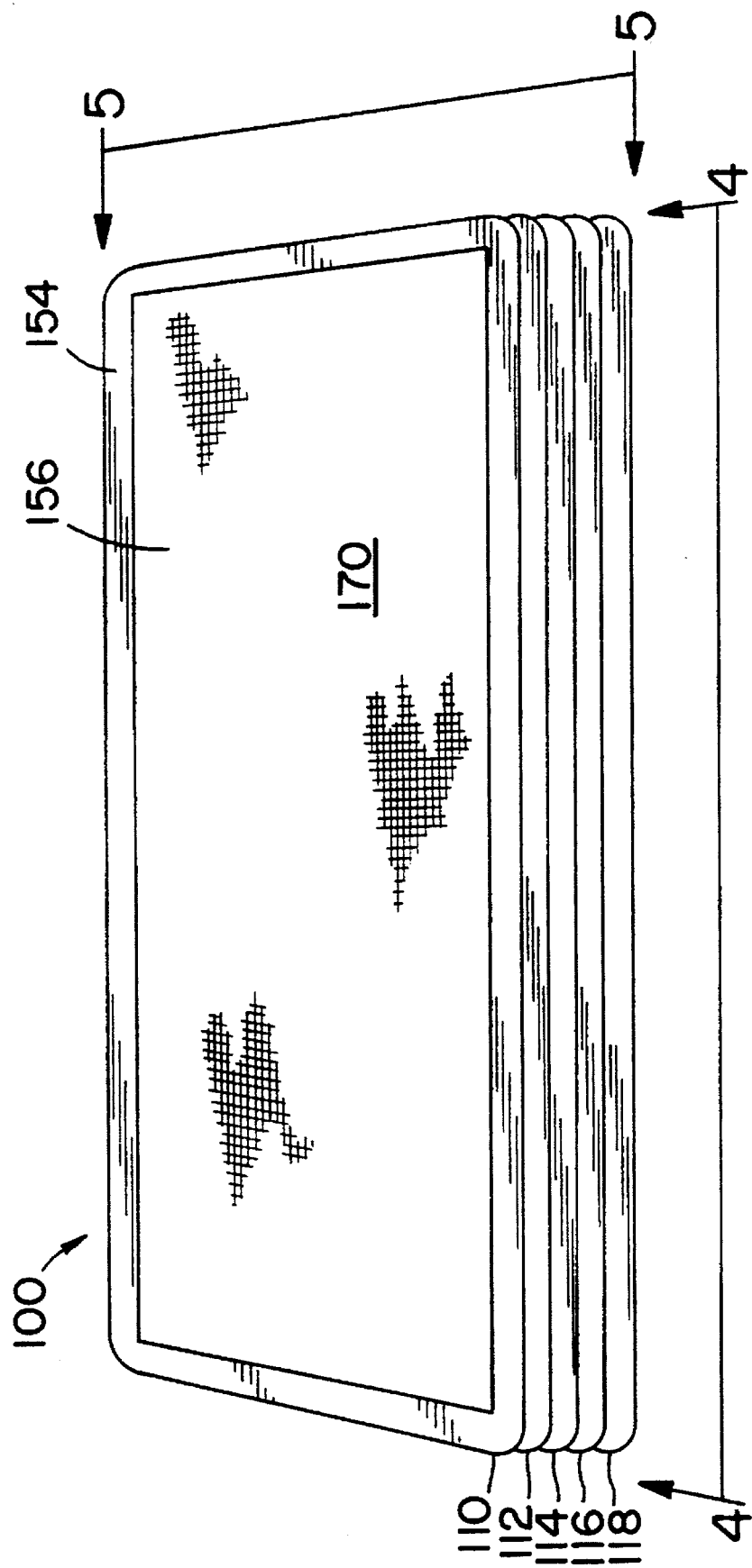
FIG. 1 is a perspective view of a multiple-unit sanitary napkin assembly constructed according to the present invention.
Figure 4:
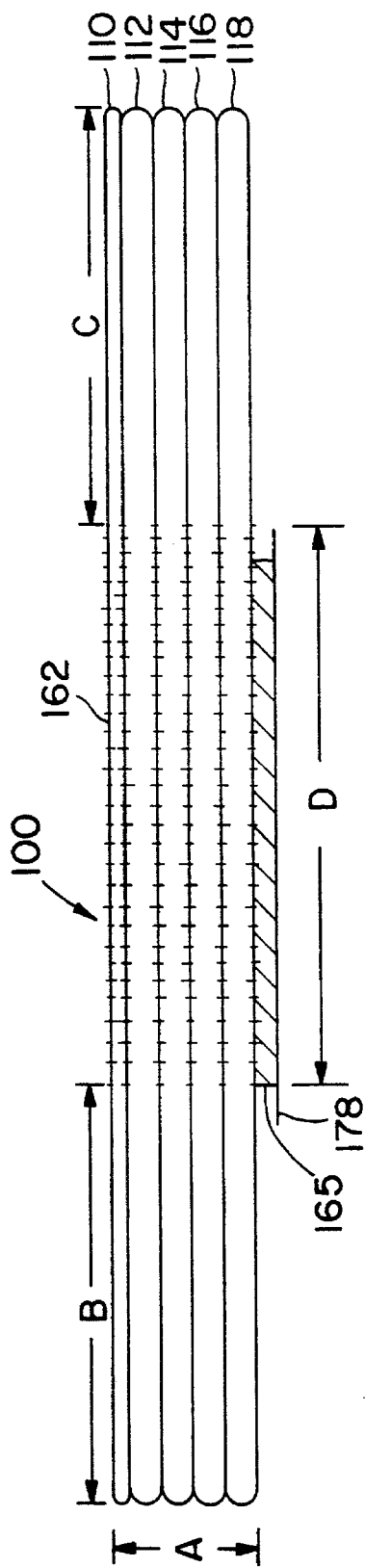
FIG. 4 is a front elevation view of the multiple-unit sanitary napkin assembly of FIG. 1.
Figure 5:
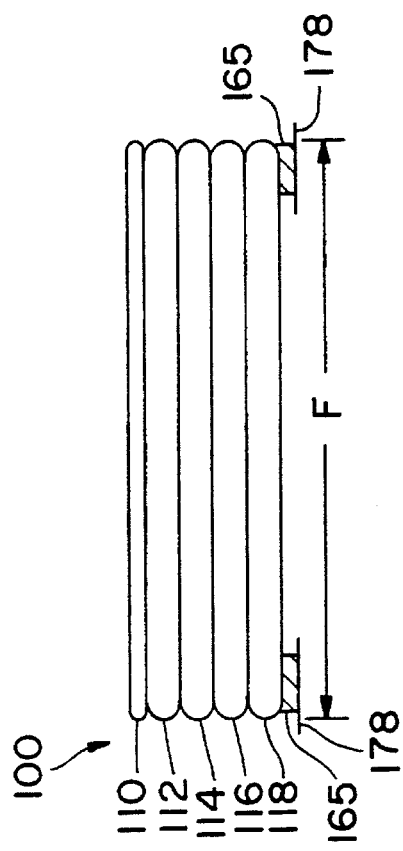
FIG. 5 is a side elevation view of the multiple-unit sanitary napkin assembly of FIGS. 1 and 4.

FIG. 1 is a perspective view of a multiple-unit sanitary napkin assembly 100 constructed according to the present invention. FIGS. 4 and 5 are front and side elevation views of the assembly 100. The assembly 100 comprises a plurality of substantially identical individual sanitary napkin units which are removably attached to one another to form a stack. The thickness of the individual units and the spacing between them are shown exaggerated in the figures for clarity. Preferably, the assembly 100 is sufficiently thin that its presence may be entirely concealed under ordinary clothing and so that the user remains comfortable during normal activities. As shown in FIG. 1, assembly 100 preferably comprises five individual units 110, 112, 114, 116, and 118, although a different number of individual units could be provided if the aforementioned conditions are satisfied.

The napkin assembly 100 is shown in FIG. 1 with the surface 170 of an uppermost individual napkin unit 110 facing upward. Surface 170 of unit 110, or an equivalent surface of another of the units, is the portion of napkin assembly 100 which is designed for contact with the user's body. Each of the individual napkin units has means 156 for receiving, absorbing, and containing body fluids secreted by the user. Each of the individual napkin units also has a barrier means 154 disposed on the side of means 156 opposite body contact surface 170 to prevent fluids received by means 156 from leaking or migrating to the other napkin units or to the user's clothing. The barrier means 154 of each of the individual napkin units is preferably permanently attached to the respective fluid receiving means 156 of that unit.

Each of the individual napkin units is preferably removably attached to the adjacent unit. In use, the entire napkin assembly 100 may be removably attached to the interior of a user's undergarment so that when the undergarment is positioned normally, the body contact surface 170 will suitably cover the fluid-emitting body region to be protected. As the user emits body fluids, they are received and absorbed in fluid receiving means 156. Barrier means 154 prevents fluids so absorbed from reaching other napkin units or the user's clothing.

When the upper-most napkin unit becomes soiled, the user may remove it from the assembly 100 for disposal, thereby exposing a fresh or unexposed napkin unit for use. The process of removing an upper-most, soiled napkin unit to expose, in turn, the next fresh unit may continue until all napkin units have been exposed. Once the last napkin unit has been used, it may be removed from the undergarment, and a new napkin assembly 100 may be removably attached thereto Removal of an uppermost napkin unit from the napkin assembly 100 is preferably accomplished by peeling the uppermost unit away from the remaining units. The materials and construction features of the individual units preferably chosen such that the uppermost unit (which may be soiled) may be conveniently removed without damaging either the unit being removed or any remaining portion of the assembly.

The fluid receiving means 156 (or a possible cover layer), is intended for direct contact with a user's skin. When a used napkin unit is removed from the assembly to expose the fluid receiving means 156 of a fresh napkin unit, it is strongly preferred that the means for attaching the removed unit to the remaining unit remain with the removed unit. This avoids irritation by preventing the attachment means from contacting the user's skin if left with the remaining unit.

Figure 2:
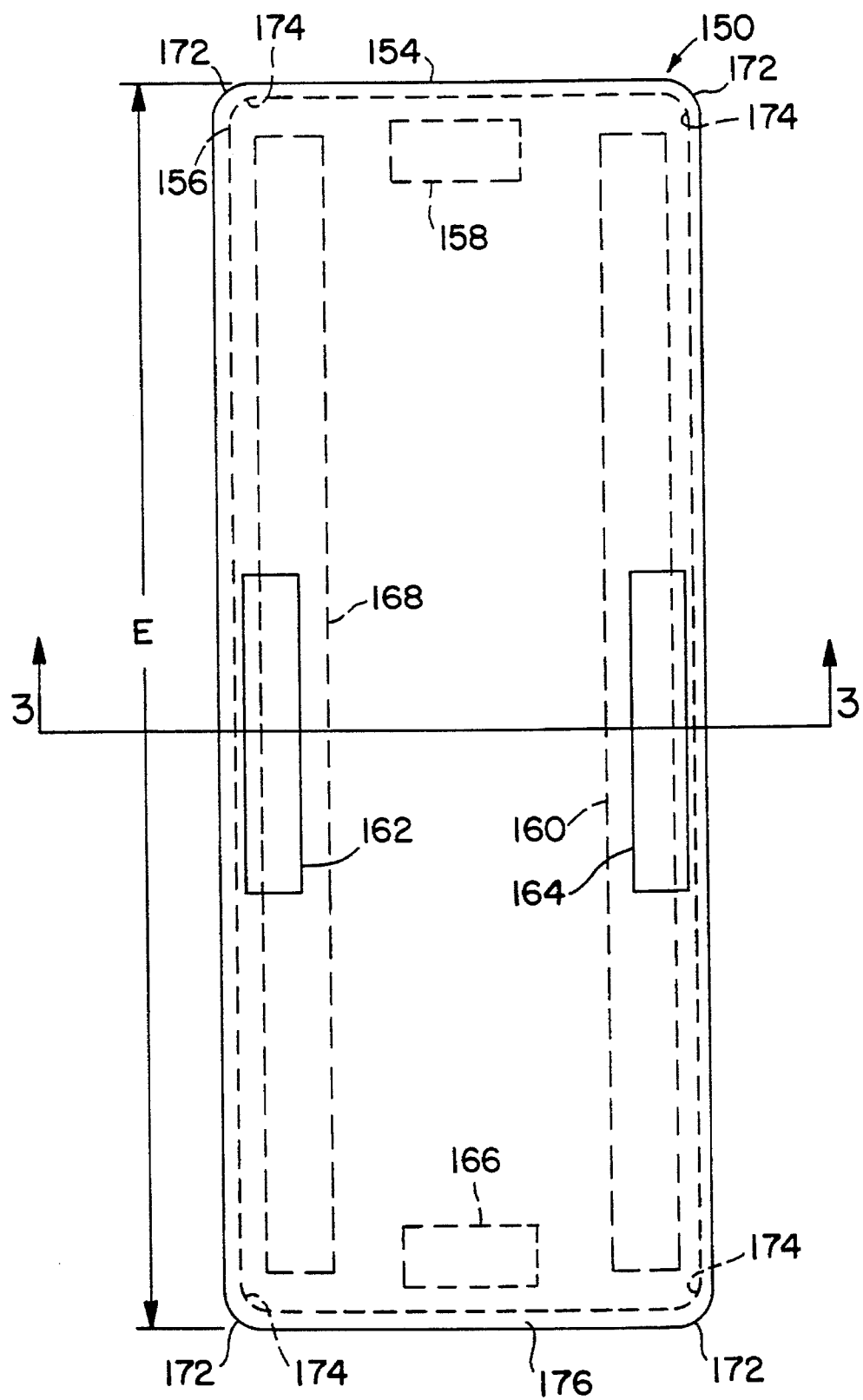
FIG. 2 is a bottom plan view of a single sanitary napkin unit which is part of the multi-unit assembly of FIG. 1.
Figure 3:
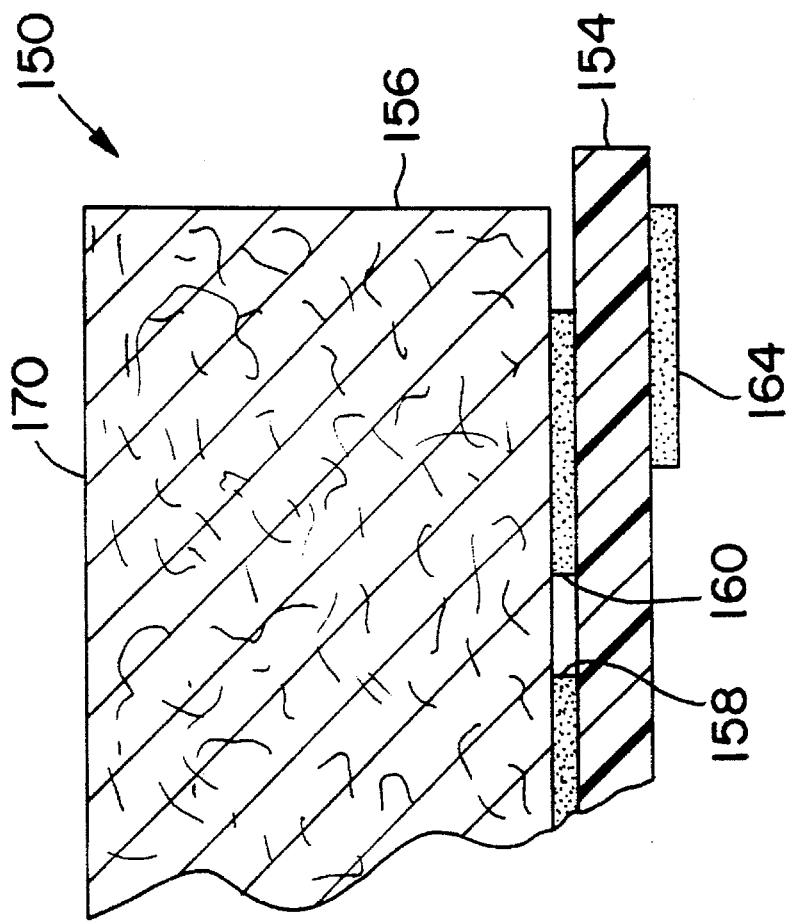
FIG. 3 is a side cross section view of the single sanitary napkin unit taken along the section lines 3—3 of FIG. 2.
Figure 3:
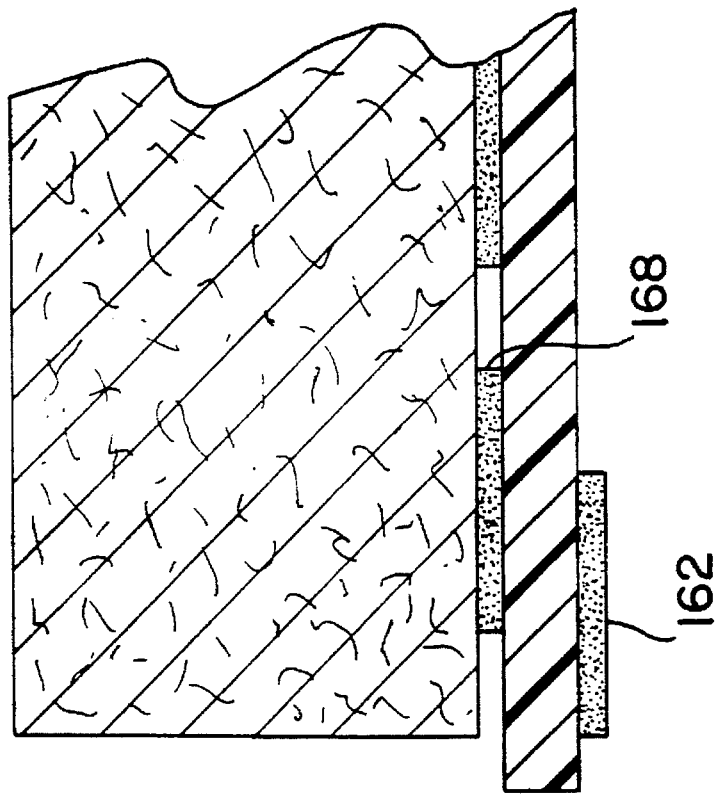

FIGS. 2–3 show construction details of an individual napkin unit 150 suitable for use in a multiple-unit sanitary napkin assembly 100 constructed according to the present invention. The vertical scale of FIG. 3 is exaggerated to show certain details. Each napkin unit has a barrier means 154 which is preferably formed from a thin, water-proof sheet or film and may be generally rectangular in shape as shown in FIG. 2. Alternatively, any other suitable shape could be selected to match the contours of the user's body in the region to be protected. For a rectangularly shaped napkin, the napkin's length, represented by dimension E (FIG. 2), is preferably approximately 5 inches, but may range from approximately 3 inches to approximately 8 inches to accommodate the size and shape of the user's body. The napkin's width, represented by dimension F (FIG. 5), is preferably approximately 2 inches, but may range from approximately 1 inch to approximately 3 inches.

The sheet or film from which the barrier means 154 is constructed is preferably soft and flexible, and may have rounded corners 172 or any other suitable corner configuration. Although the barrier means 154 is not intended, according to the invention, to be a primary surface for contact with the user's body, it is expected that extended incidental contact may occur. Therefore, the sheet or film material from which the barrier means 154 is constructed is preferably selected from materials which may safely contact the user's body without producing irritation or allergic responses. The film may be embossed with a suitable pattern to improve flexibility and provide a pleasant surface texture.

Each napkin unit also has means 156 for receiving, absorbing, and containing body fluids secreted by the user. The fluid-receiving means 156 preferably has a shape substantially identical to that of the barrier means 154. The fluid-receiving means 156 may have slightly smaller dimensions than the barrier means 154 so that a small border area 176 (FIG. 2) of the barrier means 154 is exposed around the perimeter of the fluid-receiving means 156.

The fluid-receiving means 156 is preferably absorbent and flexible. The fluid-receiving means 156 is intended for continuous contact with the user's body. Therefore, the material from which the fluid-receiving means 156 is constructed is preferably selected from materials which may safely contact the user's body without out producing irritation or allergic responses.

Appropriate means 158, 160, 166, and 168 are preferably provided to attach barrier means 154 to fluid-receiving means 156. In a preferred embodiment of the invention, primary attachment means 158, 160, 166, and 168 are thin strips of tape, bearing an adhesive on each exposed surface, which are disposed near the peripheral edges of the means 154, 156. The material selected for primary attachment means 158, 160, 166, and 168 is preferably selected from materials which may safely contact the user's body without producing irritation or allergic responses. Other primary attachment means could also be used. For example, an appropriate adhesive material, such as a glue, could be applied directly to barrier means 154 or fluid-receiving means 156.

The primary attachment means may be applied in the pattern of discrete elements of FIG. 2, or any other appropriate pattern. Alternatively, the primary attachment means could be applied as a homogeneous layer. Depending on the materials selected for barrier means 154 and fluid-receiving means 156, heat sealing or ultrasonic bonding, or a variety of other known surface treatments could also be used to attach these layers together.

Additional inter-unit attachment means 162, 164 are preferably also provided on the underside of each barrier means 154 in order to integrate a plurality of individual napkin units into the multiple-unit napkin assembly 100. In a preferred embodiment of the invention, inter-unit attachment means 162, 164 are thin strips of plastic film or tape bearing an adhesive on each exposed surface, and may be the same material selected for primary attachment means 158, 160, 166, and 168. However, other inter-unit attachment means could also be used. The inter-unit attachment means may be applied in the pattern of discrete elements of FIG. 2, or any other appropriate pattern.

The type, sizes, and configurations of inter-unit attachment means 162, 164 and the primary attachment means 158, 160, 166, and 168, are preferably co-operatively selected so that: (1) when an individual napkin unit is removed, neither that unit, nor any remaining units are damaged; and (2) only the topmost individual unit, and not any of the other units, separate from the assembly. For example, when the soiled unit is removed, it must not substantially deform or tear. Removal of a soiled unit should not cause fragmentation of the fluid-receiving means 156 of the exposed layer. Since the fluid-receiving means 156 of the exposed layer may be in direct contact with the user's skin, all of the inter-unit attachment means preferably remains with the removed napkin unit. In addition, removal of a soiled unit should not cause the fluid-receiving means of an underlying layer to separate from its barrier means.

In order to provide attachment means which perform in this manner, means are preferably provided so that the attachment formed by the primary attachment means is substantially stronger than that provided by the inter-unit attachment means. In a preferred embodiment of the invention, the inter-unit attachment means and the primary attachment means are each formed using a flexible plastic tape material. The tape material bears a suitable adhesive on each surface of the tape, and the adhesive on both surfaces may have the same strength. The desired differential between the strength of the primary attachment means and the inter-unit attachment means is accomplished by providing substantially different amounts or surface areas of the attachment means.

Accordingly, the inter-unit attachment means 162, 164 are adjacent the outside edge of the barrier means 154. The length of the inter-unit attachment means 162, 164, represented by dimension D (FIG. 4), is preferably approximately 2 inches, leaving two unattached regions of approximately 1.5 inches each, represented by dimensions B and C (FIG. 4), on either side of the primary attachment means 162, 164. The small size of the inter-unit attachment means 162, 164, compared to the primary attachment means 158, 160, 166, and 168, allows the upper-most individual unit to be removed without detaching the fluid-receiving means 156 of a lower individual unit from its respective barrier means.

It is expected that some users may be very physically active, and that occasionally an attachment may fail. If all of the attachment means were made so secure that they would not fail under any usage condition, then many users would experience difficulty in removing an individual unit from the assembly, and removal of one unit would likely damage remaining units. Further, fully secure attachments could render the assembly uncomfortable to wear. Accordingly, at least one of the attachment means of the present invention preferably are adapted to refasten or reseal themselves if an attachment fails due to temporary stress from a user's strenuous physical activity.

The napkin assembly 100 is constructed by stacking several individual napkin units. The individual napkin units are retained as an integrated assembly by the inter-unit attachment means 162, 164. Preferably, the inter-unit attachment means 162, 164 adheres more securely to the barrier means 154 than to the fluid-receiving means 156, so that when an individual napkin unit 150 is removed from the assembly 100, the inter-unit attachment means 162, 164 is automatically released from the fluid-receiving means and remains with the barrier means 154. Although it is possible that this automatic release feature could potentially fail, so that the inter-unit attachment means 162, 164 (or a part thereof) remains with the fluid-receiving means 156, the user could easily remove any remaining portion of the inter-unit attachment means by hand.

In many applications, it is desirable to secure the napkin assembly 100 to the user's undergarment. In embodiments in which the inter-unit attachment means 162, 164 is an adhesive tape strip or other similar medium, the attachment means provided on the bottom-most napkin unit may be used for this purpose. Preferably, however, special garment attachment means 165 (FIGS. 4–5) may be provided. For example, garment attachment means 165 may be implemented as two suitably placed strips of an appropriate double sided adhesive tape or two foam pads having adhesive on each side. Since the garment attachment means are not covered by any other individual napkin units, the exposed portion thereof would tend to adhere undesirably to various surfaces with which the attachment means may come into contact, such as the articles of clothing, the shipping container, etc. Accordingly, removable liners 178 (FIG. 5) are preferably provided to cover the garment attachment means 165 of the bottom-most napkin unit. The liners 178 prevent the assembly 100 from becoming inadvertently attached to garments or other objects. The liners 178 are preferably removed to expose the garment attachment means 165 before the assembly is used. Other garment attachment means could also be used. For instance, the barrier sheet of the bottom-most napkin unit could be treated with a suitable adhesive, which may be a molten adhesive.

The total thickness of the inventive sanitary napkin assembly 100, as represented by dimension A, FIG. 4, is limited so that the assembly 100 may be worn under the user's clothing without discomfort and without revealing its presence to others. For example, dimension A may preferably be limited to approximately 1.0

Various modifications to the above-described structures may be incorporated in a production embodiment. For example, other appropriate materials, such as a wet-laid or dry-laid fabric, could also be used for the fluid-receiving means 156. A top-sheet of a woven, non-woven, or "dryweave" wicking material may be provided to cover the fluid-receiving means 156. The fluid-receiving means 156 may be replaced with a super-absorbent material, or special chemicals may be added to the fluid-receiving means to enhance its absorbent capacity, as is known in the art. Other chemicals may be added to control odor. In addition, a polyethylene sheet could be used for the barrier means 154. The configuration of the garment attachment means may vary in a production embodiment. For example, a single, large adhesive pad may be provided instead of the two smaller pads described above.

The selection of appropriate materials for constructing the napkin assembly 100 of the present invention is important in enabling the assembly to accomplish several objectives. Individual units must be highly absorbent without being bulky. It is highly desirable to provide individual units 150 which remain substantially intact from the time the napkin assembly is first put to use, through removal and disposal of the individual unit. It is also highly desirable to provide an assembly 100 which remains substantially intact throughout use, but permits individual units thereof to be removed conveniently without ripping, tearing, or otherwise damaging that unit or any remaining units.

The term "substantially" intact refers to the fact that under heavy use, such as when the user engages in physical work or athletic activity, the assembly will be subject to large amounts of stress, and that one or more of the attachment means may temporarily detach. It is therefore desirable to provide attachment means which are forgiving of temporary stress and if detached, may automatically reattach themselves. Thus, even if the user engages in fairly rigorous physical activity, the assembly will not become inoperative. It is also important to properly select materials and construction features for the individual units so that they may be disposed of safely in conventional plumbing systems.

A prototype embodiment of the invention employing the materials described herein has been constructed and tested and has been found to perform acceptably. However, other materials could also be used within the scope of the present invention. A number of material selection tradeoffs are presented to illustrate the range of material specifications which may be used.

A suitable material for the barrier means 154 is an embossed polypropylene sheet having a thickness of approximately 0.0006 inches. Such material is available from Clopay Plastic Products Division, 101 E. Fourth St., Cincinnati, Ohio, 45202, as TAFFAFLEX embossed Type X polypropylene sheet. Other materials may also be suitable.

The polypropylene sheet preferably has an electrical surface treatment of about 40 dynes per cm on one side of the sheet. Commercially available surface treatments range from around 25 to 42 dynes per cm and may be applied to one or both surfaces of the polypropylene sheet. Thus, this energy range is at or near the upper end of the available range of surface treatments for commercially available polypropylene sheets. When used with certain adhesives, this surface treatment is believed to increase the attachment strength of the adhesive to the treated side of the polypropylene sheet, and possibly, to reduce the attachment strength of the adhesive to other materials near the sheet. When constructing an individual unit, inter-unit attachment means is applied to the treated side of the sheet, and the primary attachment means is applied to the untreated side of the sheet.

A suitable material for fluid-receiving means 156 is a two-ply air-laid fabric constructed of wood-pulp fibers and having; a thickness of approximately 0.145 inches. Such material is available from James River Corporation, Green Bay Mill, Green Bay, Wis. 54305, as AIRTEX air-laid fabric, Specification 399. This material has an average bone-dry basis weight of 97.3 grams per square meter (59.8 pounds per ream), an average 2-ply caliper of 145 mils, and an average water absorbency or "wick" rate of 0.6 sec per milliliter. A binder material of vinyl-acetate-ethylene latex is used. This material is believed to be particularly advantageous for use in this application because it provides high bulk and loft, large pores, high absorbent capacity, and is comprised of low density, loosely compacted fibers. The material is hypo-allergenic and can be safely used in contact with the skin. These features provide a fluid-receiving means 156 which is suitably absorbent, and they promote safe disposal in conventional plumbing systems. Other materials may also be suitable.

A suitable material for primary attachment means 158, 160, 166, and 168, and for inter-unit attachment means 162, 164 is double-coated polyethylene tape having a thickness of 0.005 inches. Such material is available from 3M Health Care, St. Paul, Minn. 55144, under product specification No. 1509. The tape has a tensile strength of 5 pounds/inch (22.3 n/inch) and an elongation of 200 percent.

This material is coated on each side with a pressure-sensitive acrylic adhesive. The adhesive strength of this tape (specified with respect to steel) is specified at 9.7 Newtons/in. Double-coated tapes generally available for use in medical applications have a range of adhesive strength of approximately 2.22 Newtons/in to 11.11 Newtons/in. Thus, the adhesive strength of the preferred material is relatively high. While this strength of adhesion is important in keeping the assembly of shields together, it should also be noted that it does not cause fragmentation of the air laid fabric onto the tape upon removal of the uppermost shield. The chemistry of the adhesive may promote the clean removal of the tape from the air-laid fabric of fluid-receiving means 156 and enhance the bond with the polypropylene sheet of barrier means 154.

A set of experiments has been conducted which reveal an unexpected synergistic cooperation between the preferred materials for the barrier means 154, fluid receiving means 156, primary attachment means 158, 160, 166, and 168, and inter-unit attachment means 162, 164. In these trials, a clean sheet of glass was prepared. Samples of the double coated adhesive tape were formed having dimensions ¼ inch by ⅛ inch. Samples of the polypropylene barrier sheet and the air-laid fluid receiving sheet were formed, having dimensions of 5 inches by 2 inches.

In a first set of trials, a sample of adhesive tape was first applied to the glass. A sample of the air-laid sheet was then pressed to the adhesive tape, and removed. The samples were inspected to determine: (1) whether the adhesive tape adhered to the glass or to the air-laid sheet; and (2) whether the air-laid sheet was damaged or fragmented. In each of 20 trials, the adhesive tape adhered to the glass, and the air-laid sheet was severely deformed and fragmented.

In a second set of trials, a sample of adhesive tape was first applied to a sample air-laid sheet. The sample of the air-laid sheet was then pressed to the glass with the adhesive tape facing the glass, and removed. The samples were inspected to determine: (1) whether the adhesive tape adhered to the glass or to the air-laid sheet; and (2) whether the air-laid sheet was damaged or fragmented.

In each of 20 trials, the adhesive tape again adhered to the glass, and the air-laid sheet was again severely deformed and fragmented.

In a third set of trials, a sample of adhesive tape was first applied to the glass. A sample of the polypropylene sheet was then pressed to the adhesive tape, and removed. The samples were inspected to determine: (1) whether the adhesive tape adhered to the glass or to the polypropylene sheet; and (2) whether the polypropylene sheet was damaged or deformed. In each of 20 trails, the adhesive tape adhered (transferred) to the polypropylene, and the polypropylene sheet was not deformed or damaged.

In a fourth set of trials, a sample of adhesive tape was first applied to a sample polypropylene sheet. The sample of the polypropylene sheet was then pressed to the glass with the adhesive tape facing the glass, and removed. The samples were inspected to determine: (1) whether the adhesive tape adhered to the glass or to the polypropylene sheet; and (2) whether the polypropylene sheet was damaged or deformed. In each of 20 trails, the adhesive tape again adhered to the polypropylene, and the polypropylene sheet was not deformed or damaged.

Other trials were conducted with the adhesive tape first applied to the untreated side of the polypropylene sheet. The tape adhered (transferred) to the glass and the polypropylene was deformed. In still other trials, the adhesive was first applied to the glass and then the untreated side of the polypropylene was pressed and removed. The adhesive tape remained with the glass and deformation was observed. It should be noted single-surface treatments can cause ionic transfer (i.e., can affect the untreated side of the sheet) if not properly contained.

In other trials, sanitary napkin assemblies were constructed according to the present invention. Individual units were removed from the assembly in series. The individual units were inspected to determine whether the inter-unit attachment adhered to the air laid fluid-receiving sheet or to the polypropylene barrier sheet, and whether the air laid sheet was damaged or fragmented. In each trial, the inter-unit attachment adhered to the polypropylene barrier sheet, and the air laid-sheet was either completely unaffected, or extremely minimal fragmentation occurred.

These experiments show that the adhesive tape adheres more strongly to the polypropylene barrier sheet than to clean glass, and adheres more strongly to the polypropylene barrier sheet than to the air-laid fluid-receiving sheet.

Further, when the tape was used to attach an air-laid sheet to a glass substrate, the adhesive tape adhered to the air-laid sheet significantly, so that when the air-laid sheet was removed, it deformed and fragmented. In contrast, when the tape was used to attach an air-laid sheet to a polypropylene barrier sheet substrate, the adhesive tape did adhere significantly to the polypropylene barrier sheet substrate, so that when the air-laid sheet was removed, virtually no deformation or fragmentation occurred. Thus, the presence of the polypropylene barrier sheet caused the adhesive of the specified tape to release more easily from the air laid sheet.

This is an unexpected synergistic effect of the combination of the particular materials selected for the barrier means 154, fluid receiving means 156, and various attachment means. The experiments show that the inter-unit attachment means does not transfer onto the air laid fabric upon removal of the uppermost shield, nor does it fragmentationally detach from the air laid fabric.

This is advantageous for at least three reasons. First, if the adhesive attachment to the air laid sheet was stronger than the attachment to the polypropylene sheet, then removal of the uppermost unit would leave the adhesive on the fluid receiving means of the next available shield. This would be undesirable due to the close proximity of the adhesive to sensitive areas of the body. Second, deformation of the fluid receiving means beneath would affect that unit's absorbent capacity, would be visibly defective and could render the entire assembly unusable. Third, if the fluid receiving means fragments onto the tape adhesive, the adhesive capacity and strength of the tape are reduced.

This particular combination of materials enables an individual unit to be removed with ease and without deformation or fragmentation of the fluid receiving means. A clean separation and removal of the top-most unit enables the integrity of both the fluid-receiving means and the attachment means to be maintained. In addition, this combination of materials renders the attachment means of the present invention refastenable. If another attachment means which permits or causes fragmentation of the fluid receiving means onto the attachment is used, then the adhesive capacity would be lowered, and a refastenable system would not be achieved.

Preferably, the construction materials for each of the individual sanitary napkin units 150 are selected for compatibility with conventional plumbing systems to permit the individual napkin units 150 to be safely disposed of in ordinary water closets. Prototype embodiments of sanitary napkin units 150 constructed according to the preferred specifications noted above have been tested and meet this requirement. Variations in size and material may affect disposal requirements or functional performance.

Each individual unit 150 may be flushed into a domestic plumbing system without damaging or clogging plumbing fixtures, drain lines, or sewers. When flushed, the individual units 150 preferably remain substantially intact and have approximately neutral buoyancy. This enables the individual unit to be carried along with other waste in a moving stream of wastewater. Although flushable sanitary products, such as various forms of bathroom tissue, are known, these products are generally formed from extremely thin sheets of a porous, homogeneous material, and are generally intended to disintegrate in the waste stream.

In contrast to the prior art, the individual units 150 of the present invention are thicker and are constructed of at least two different materials. Therefore, in contrast to the prior art, the materials and construction of the individual units 150 of the present invention are preferably selected to achieve an individual unit which, as a whole, provides approximately neutral buoyancy and which tends to discourage disintegration.

The water absorbency or wick rates described below for several materials is obtained by a "Wick Test." A 1 ml sample of water is poured from a pipette held 3 inches above an 8-½ inch by 11 inch sheet of the material, and the rate at which the water wicks through the material is observed. Wick rates in typical sanitary article materials range from around 0.5 sec/ml to about 2.0 sec/ml. A typical paper towel may have a wick rate of approximately 1.2 sec/mi. A typical baby paper towel or baby wash cloth may have a wick rate of approximately 2 sec/ml.

The wick rate of a preferred commercially available material which may be used to construct the fluid-receiving means 156 of the present invention is 0.6 seconds per milli-liter (sec/ml). Thus, the preferred material wicks substantially more rapidly than both paper towels and baby paper wash cloths. This high wick rate improves the flushability of the individual units 150 by promoting rapid absorption of water, so that upon disposal, the unit almost immediately achieves the desired nearly neutral buoyancy.

In addition, the preferred material for fluid-receiving means 156 has large voids and pores. The voids are open areas between the latex and the fibrous material. The large pores and voids promote a high wick rate, as desired. Because the pores and voids of the preferred material are large, compared to more compact materials, the preferred material has excellent absorbent capacity, and will hold 17 grams of water per 1 gram of substrate, under no force.

The density of the preferred material also improves its performance when disposed by flushing. The density of the material may be determined by dividing the basis weight of the material by its thickness or caliper. A typical panty shield may have a weight as low as 30 pounds per ream. In contrast, a preferred material for constructing the fluid-receiving means 156 may have a weight of 60 pounds per ream. Both the weight and thickness of the preferred material promote flushability. The large size of the pores and voids of this material improve the wick rate, and increase the absorbent capacity. All of these factors affect the flushability of the individual units, and certain variations may defeat flushability. As a result, material selection is highly important in achieving an individual unit with satisfactory disposal performance in conventional plumbing systems.

For example, the wick rate and absorbent capacity decrease as pore size decrease. If the pore size were smaller but the weight remained the same, there is no guarantee that the individual unit 150 would flush satisfactorily in conventional plumbing systems. Similarly, if the material density were reduced to approximately 30 pounds per ream, there is no guarantee the individual unit 150 would flush satisfactorily, even if the pore size were enlarged.

Many prior art products, which are intended to be flushed through conventional plumbing systems, are also intended to disintegrate into tiny particles. However, it is noted that the size of an object, or its ability to disintegrate, does not necessarily determine whether it may be flushed. There are many items which cannot be safely flushed, even through they are small or, by their nature, would appear to disintegrate in a plumbing system. Paper liners, paper towels, baby paper towels and wash cloths, and even small cigarette butts are just a few examples of items which cause significant problems when flushed into plumbing systems. Public restrooms and sanitary product containers typically warn users against disposing of such products in water closets or similar waste streams. Often, public restrooms provide special receptacles for sanitary waste items which should not be flushed but also should not be disposed of as ordinary refuse.

The following table compares the characteristics of the preferred material for fluid-receiving means (AIRTEX 399) to some commonly available products:

| Material | Wick Rate | Absorbent Capacity | Pore Size | Density |
|---|---|---|---|---|
| AIRTEX 399 | Fast | High | Large | Low |
| Paper Towel | Medium | Medium | Medium | Medium |
| Baby Paper Towel or Wash Cloth | Slow | Low | Small | Heavy |

Flushability is largely determined by density, volume and bulkiness. The present invention optimizes and balances these criteria. A wide range of materials might also satisfy these criteria in a different way, e.g. lower density, lower or higher volume and bulkiness, etc., but might not be functional in an assembly of sanitary napkins. Other materials having characteristics in the range between the preferred AIRTEX 399 non-woven fabric and a paper towel would potentially be flushable, and may be usable in this application.

Flushability is determined by buoyancy in water. The performance of an item when flushed improves as the buoyancy of the item approaches neutrality in water. The following calculation indicates the approximate density of the preferred material for the fluid-receiving means (AIRTEX 399):

Notes:
a. the density of water is 1 gram per cc or cubic centimeter;
b. 1 mil=1/1000 in;
c. 1 meter=100 cm; and
d. 1 in=2.54 cm.

$$\text{Density} = \frac{\text{Weight}}{\text{Caliper}}$$

$$\text{Weight} = 97.3 \frac{g}{m^2}$$

$$\text{Caliper} = 145 \text{ mils}$$

$$\left(97.3 \frac{g}{m^2}\right) \left(\frac{1 m}{100 cm}\right) \left(\frac{1 m}{100 cm}\right) = 0.00973 \frac{g}{cm^2}$$

$$(145 \text{ mils}) \left(0.001 \frac{in}{mil}\right) \left(2.54 \frac{cm}{in}\right) = 0.36830 \text{ cm}$$

$$\text{Density of air-laid fabric} = \frac{\left(0.00973 \frac{g}{cm^2}\right)}{0.36830 \text{ cm}} = 0.0264 \frac{g}{cm^3}$$

The preferred materials described herein have been tested and appear to function well in the inventive sanitary napkin assembly, and also provide acceptable performance when disposed of by flushing in conventional domestic plumbing systems. However, variations in the specifications of the preferred materials may provide acceptable product function without degrading disposal performance.

As a result of the multiple individual napkin units provided by the inventive sanitary napkin assembly 100, a comparatively large total absorptive capacity is achieved. The user may conveniently dispose of soiled individual units as required, thereby maximizing comfort and protection by making a fresh unit immediately available. In contrast to prior art sanitary napkins, the user need not separately carry fresh units. Because of the large absorptive capacity, the assembly 100 may provide protection for a long period of wear. This feature, in conjunction with the ability to dispose of individual napkin units in conventional water closets, maximizes convenience for users when limited privacy is available.

The above-described embodiment of the invention is merely one example of a way in which the invention may be carried out. Other ways may also be possible, and are within the scope of the following claims defining the invention.

What is claimed is:

1. An integrated sanitary napkin assembly comprising at least two individual sanitary napkin units, said individual units being disposed serially adjacent to one another and removably attached to one another;

at least one of said individual units being adapted to be removed from said assembly, leaving at least one of said units of said assembly remaining;

at least one of said individual units having:

means for receiving body fluids secreted by a user; fluid impervious barrier means disposed substantially adjacent said body fluid receiving means; an intra-unit attachment means joining said barrier and said body-fluid receiving means for attaching the barrier means to said body-fluid receiving means; and inter-unit attachment means for attaching said individual unit to an adjacent unit;

said fluid impervious barrier means defining at least one barrier means peripheral edge, said body fluid receiving means defining at least one receiving means peripheral edge, said barrier means peripheral edge and said receiving means peripheral edge each having a length, the barrier means peripheral edge and the receiving means peripheral edge being disposed substantially adjacent one another in said individual unit;

said intra-unit attachment means contacting said body fluid receiving means and said fluid impervious barrier means and extending adjacent said peripheral edges thereof for a substantial fraction of said lengths of said peripheral edges;

each of said individual units defining at least one individual-unit peripheral edge, each such individual-unit peripheral edge having a length, the individual-unit peripheral edges of said at least two individual units being disposed substantially adjacent one another in said assembly;

said inter-unit attachment means contacting said at least two individual units and extending adjacent said individual-unit peripheral edges of said units for a substantial fraction of said length of said individual-unit peripheral edges.

2. An integrated sanitary napkin assembly comprising at least two individual sanitary napkin units, said individual units being disposed serially adjacent to one another and removably attached to one another;

at least one of said individual units being adapted to be detached from said assembly, leaving at least one of said units of said assembly remaining;

at least one of said individual units having:

means for receiving body fluids secreted by a user; fluid impervious barrier means disposed substantially adjacent said body fluid receiving means; an intra-unit attachment means joining said barrier and said body-fluid receiving means for attaching the barrier means to said body-fluid receiving means; and inter-unit attachment means for attaching said individual unit to an adjacent unit;

each of said individual units defining at least one individual-unit peripheral edge, said inter-unit attachment means contacting said at least two individual units and extending adjacent said individual-unit peripheral edges of said units;

said inter-unit attachment means comprising releasable adhesive means, said adhesive means retaining its adhesive quality even after release, whereby said inter-unit attachment means may operate after said at least one individual unit has been detached to re-attach said individual unit to any remaining units of said assembly.

3. An integrated sanitary napkin assembly comprising at least two individual sanitary napkin units, said individual units being disposed serially adjacent to one another and removably attached to one another;

at least one of said individual units being adapted to be detached from said assembly, leaving at least one of said units of said assembly remaining;

at least one of said individual units having:

means for receiving body fluids secreted by a user; fluid impervious barrier means disposed substantially adjacent said body fluid receiving means; an intra-unit attachment means attaching the barrier means to said body-fluid receiving means; and inter-unit attachment means for attaching said individual unit to an adjacent unit;

said individual unit exhibiting a density when said individual unit is immersed in fresh water; said body fluid receiving means, said fluid impervious barrier means, and said attachment means cooperating such that, as a whole, said density of said individual unit approximates the density of fresh water; whereby said individual unit has substantially neutral buoyancy in fresh water.

4. An integrated sanitary napkin assembly comprising at least two individual sanitary napkin units, said individual units being disposed serially adjacent to one another and removably attached to one another;

at least one of said individual units being adapted to be removed from said assembly, leaving at least one of said units of said assembly remaining;

at least one of said individual units having:

means for receiving body fluids secreted by a user; fluid impervious barrier means disposed substantially adjacent said body fluid receiving means; an intra-unit attachment means joining said barrier and said body-fluid receiving means for attaching the barrier means to said body-fluid receiving means; and inter-unit attachment means for attaching said individual unit to an adjacent unit;

each of said individual units defining at least one individual-unit peripheral edge, each such individual-unit peripheral edge having a length, the individual-unit peripheral edges of said at least two individual units being disposed substantially adjacent one another in said assembly;

and said inter-unit attachment means contacting said at least two individual units and extending adjacent said individual-unit peripheral edges of said units for a substantial fraction of said length of said individual-unit peripheral edges.

5. The article of claim 4 wherein said intra-unit attachment means is formed from an adhesive applied to at least one of said body fluid receiving means and said fluid impervious barrier means.

6. The article of claim 4 wherein said intra-unit attachment means is formed from at least one strip of adhesive tape applied to at least one of said body fluid receiving means and said fluid impervious barrier means.

7. The article of claim 4 wherein said intra-unit attachment means comprises glue applied to at least one of said body fluid receiving means and said fluid impervious barrier means.

8. The article of claim 4 wherein said intra-unit attachment means is formed from a region wherein said body fluid receiving means and said fluid impervious barrier means are crimped together.

9. The article of claim 4 wherein said intra-unit attachment means is formed as a region wherein said body fluid receiving means and said fluid impervious barrier means are joined by thermal bonding.

10. The article of claim 4 wherein said intra-unit attachment means is formed as a region wherein said body fluid receiving means and said fluid impervious barrier means are joined by ultrasonic bonding.

11. The article of claim 4 wherein said intra-unit attachment means is formed as a pattern of plural discrete elements.

12. The article of claim 4 wherein said intra-unit attachment means is formed as a homogeneous layer.

13. The article of claim 4 having means for attaching said assembly to a user's garment, said garment attachment means comprising an adhesive layer applied to a surface of said fluid impervious barrier means, said surface fluid impervious barrier means having an area, and said adhesive layer being applied to said surface over a substantial fraction of said area.

14. The article of claim 4 having means for attaching said assembly to a user's garment, said garment attachment means comprising an adhesive layer applied to a surface of said fluid impervious barrier means, and said adhesive layer being applied to said surface in a molten state.

15. The article of claim 4, said at least one individual unit further comprising porous barrier means for permitting transmission of body fluids from said user to said body-fluid receiving means while avoiding contact between said user and said body-fluid receiving means.

16. The article of claim 15 wherein said porous barrier means comprises a woven sheet material.

17. The article of claim 15 wherein said porous barrier means comprises a non-woven sheet material.

18. The article of claim 15 wherein said porous barrier means comprises a dry-weave sheet material.

19. The article of claim 4 wherein said fluid impervious barrier means comprises a polyethylene sheet.

20. The article of claim 4 wherein said body fluid receiving means comprises a wet-laid fabric material.

21. The article of claim 4 wherein said body fluid receiving means comprises a dry-laid fabric material.

22. The article of claim 4 wherein said body fluid receiving means comprises a super-absorbent material.

23. The article of claim 4 wherein said body fluid receiving means comprises an absorbent material treated to enhance absorbent capacity.

24. The article of claim 4 wherein said body fluid receiving means comprises an absorbent material treated to control odor.

* * * * *

UNITED STATES PATENT AND TRADEMARK OFFICE
CERTIFICATE OF CORRECTION

PATENT NO. : 5,613,964
DATED : March 25, 1997
INVENTOR(S) : Grenier

It is certified that error appears in the above-indentified patent and that said Letters Patent is hereby corrected as shown below:

Col. 4, Ln. 9, delete "thereto removal" insert --thereto. Removal--

Col. 6, Ln. 7, delete "primary attachment means"
insert --inter-unit attachment means--

Col. 7, Ln. 3, delete "approximately 1.0" insert --approximately 1.0 inch--

Signed and Sealed this

Twenty-seventh Day of January, 1998

Attest:

BRUCE LEHMAN

*Attesting Officer*  *Commissioner of Patents and Trademarks*